United States Patent [19]
Kuehn

[11] 3,954,714

[45] May 4, 1976

[54] POLYMERIZABLE URETHANE COMPOUNDS AND POLYMERS THEREOF

[75] Inventor: Erich Kuehn, Wilmington, Del.

[73] Assignee: ICI United States Inc., Wilmington, Del.

[22] Filed: Sept. 9, 1974

[21] Appl. No.: 504,550

Related U.S. Application Data

[62] Division of Ser. No. 211,670, Dec. 23, 1971, Pat. No. 3,856,830.

[52] U.S. Cl. .................. 260/47 CZ; 260/47 CB; 260/77.5 BB; 260/859 R; 260/859 PV
[51] Int. Cl.² ................................ C08G 18/32
[58] Field of Search .... 260/47 CZ, 47 CB, 77.5 BB, 260/859 R, 859 PV

[56] References Cited
UNITED STATES PATENTS

| | | | |
|---|---|---|---|
| 3,297,745 | 1/1967 | Fekete et al. | 260/347.4 |
| 3,509,234 | 4/1970 | Burlant et al. | 260/859 R |
| 3,592,784 | 7/1971 | Brack | 260/77.5 BB |
| 3,644,569 | 2/1972 | Pietsch et al. | 260/858 |
| 3,719,638 | 3/1973 | Huemmer et al. | 260/859 R |
| 3,772,404 | 11/1973 | Knight et al. | 260/859 R |
| 3,778,408 | 12/1973 | Burns et al. | 260/47 CB |

*Primary Examiner*—M. J. Welsh

[57] ABSTRACT

Ethylenically unsaturated urethane monomers containing three or more double bonds per molecule and addition polymers and copolymers of these compounds are disclosed.

7 Claims, No Drawings

POLYMERIZABLE URETHANE COMPOUNDS AND POLYMERS THEREOF

This application is a division of my copending application, Ser. No. 211,670, filed Dec. 23, 1971 now U.S. Pat. No. 3,856,830.

This invention relates to ethylenically unsaturated monomers, the homopolymers and copolymers of these monomers, and mixed resins prepared from these monomers and unsaturated polyesters. More particularly, this invention relates to ethylenically unsaturated monomers prepared from unsaturated hydroxyl terminated esters, and polyisocyanates containing at least about three isocyanate groups per molecule, and the homopolymers and copolymers as well as mixed resins prepared using these monomers.

It is an object of this invention to provide ethylenically unsaturated monomers containing at least three double bonds.

It is another object of this invention to provide novel polymers from ethylenically unsaturated monomers containing at least three double bonds.

It is another object of this invention to provide homopolymers and mixed resins suitable for forming molded plastic products and fiber reinforced plastic products and laminates prepared by using an ethylenically unsaturated monomer containing at least three double bonds.

These and still other objects of this invention will become apparent to those skilled in the art from the following detailed disclosure of this invention.

The novel ethylenically unsaturated monomers (monomer resins) of this invention are comprised of the reaction product of (a) an organic polyisocyanate having at least 3 isocyanate groups, and (b) a stoichiometric quantity of a hydroxyl terminated ethylenically unsaturated ester for reacting with each of said isocyanate groups. A preferred group of monomers of unsaturated urethane compounds may be represented by the formula:

(1)
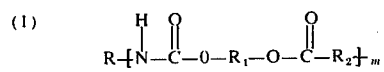

wherein R is a residue of a polyfunctional organic isocyanate which contained at least $m$ isocyanate groups, $m$ is at least about 3, $R_1$ is selected from the group consisting of alkylene radicals which contain at least 2 carbon atoms, a radical resulting from the removal of 2 hydroxyl groups from a cycloaliphatic diol, a radical resulting from the removal of 2 hydroxyl groups from an etherified diphenol and a radical resulting from the removal of 2 hydroxyl groups from an ethylenically unsaturated diol and $R_2$ is an alkenyl radical containing from about 3 to 18 carbon atoms, provided that the sum of the carbon atoms in $R_1$ and $R_2$ is from about 5 through about 48.

Novel homopolymers and copolymers of the present invention are prepared by the polymerization of monomers within the formula represented above with or without other ethylenically unsaturated monomers in the presence of or absence of free radical catalysts.

Among the mixed resins of this invention are those comprised of the addition polymerization products of the ethylenically unsaturated monomer represented by the above Formula (1) and an ethylenically unsaturated polyester resin. The polyester resin can be the condensation product of an unsaturated dicarboxylic acid and an etherified diphenol which can be represented by the formula (2)

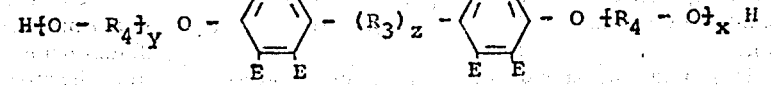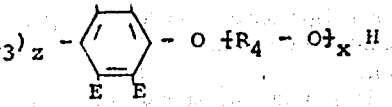

wherein $z$ is 0 or 1; $R_3$ is an alkylene radical containing from 1 to 5 carbon atoms, oxygen, sulfur, or a divalent radical which may be represented by the following formula

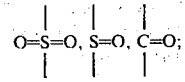

$R_4$ is ethylene or propylene; each E is individually selected from hydrogen atoms and halogen atoms; and $x$ and $y$ are integers from 1 through about 20 with the proviso that the sum of $x$ and $y$ is from about 2 through about 30. Any of the well known suitable ethylenically unsaturated dicarboxylic acids can be used to prepare the present polyester resins by condensation with a diol represented by Formula (2). For example among those acids that can be used are maleic acid, fumaric acid or the anhydride of maleic acid. Examples of compounds within the above general Formula (2) are polyoxypropylene(2)-2,2-bis(4-hydroxyphenyl) propane; polyoxyethylene(3)-2,2-bis(4-hydroxyphenyl) propane; polyoxypropylene(3)-bis(4-hydroxyphenyl) thioether; polyoxy-ethylene(2)-2,6-dichloro-4-hydroxyphenyl 2',3',6'-trichloro-4'-hydroxyphenyl methane; polyoxypropylene(3)-2-bromo-4-hydroxy-phenyl 4'-hydroxyphenyl ether; polyoxyethylene(2.5)-4,4'-isopropylidenediphenol; polyoxybutylene(4)-bis(4-hydroxyphenyl) ketone; polyoxypropylene(3)-2,2-bis(2,6-diiodo-4-hydroxyphenyl) propane; and polyoxypropylene(2.2)-2,2-bis(4-hydroxyphenyl) propane.

As stated above the present urethane monomers represented by Formula (1) above are polymerizable with ethylenically unsaturated polyesters. In addition to polyesters prepared from the above described diol and dibasic acid reactants other suitable ethylenically unsaturated polyester resins can be prepared from either an ethylenically unsaturated dicarboxylic acid and a saturated diol, or an ethylenically unsaturated diol and a saturated dicarboxylic acid, or both the diol and the dicarboxylic acid can be ethylenically unsaturated. Among the additional diol reactants that can be used are the straight or branched chain alkane diols and the cycloaliphatic diols as well as such diols that are halogen substituted having from 2 to 12 carbon atoms.

Unsaturated aliphatic diols containing from 2 to 10 carbon atoms can also be used. For example among the diols that can be used are ethylene glycol, 1,4-butylene glycol, 1,6-hexylene glycol, neopentyl glycol, 1,4-cyclohexanedimethanol, 2,5-dimethyl-2,5-hexanediol, and the monoallyl ether of glycerin. Among the other acids that can be used to prepare the subject polyester resins are o-phthalic acid, isophthalic acid, adipic acid, sebacic acid, succinic acid and azelaic acid. Suitable halogenated derivatives of such acids can also be used to prepare the subject unsaturated polyester resins. Examples of the polyesters contemplated as useful in preparing mixed resins with the urethane monomers of this invention are the following: neopentyl glycol fumarate, propylene glycol maleate, dibromobutenediol succinate, polyoxypropylene(16)-2,2-bis(4-hydroxyphenyl)propane fumarate, and polyoxyethylene(2.2)-2,2-bis(2,6-dichloro-4-hydroxyphenyl)propane fumarate.

In general the above noted unsaturated polyester resins can be prepared by reacting a suitable dicarboxylic acid with a suitable diol such as one of the above described etherified diphenols at a temperature of about 200° C. or more under an inert atmosphere. Known catalysts or promoters used in preparing polyesters, for example p-toluenesulfonic acid, can be added in catalytic amounts to enhance the activity of the particular reactants if indicated. Suitable catalysts, for example p-toluenesulfonic acid is used at a concentration of from about 0.005% to 0.3% by weight based on the weight of the reaction mixture. The ratio of the number of hydroxyl groups of said diol to the number of carboxyl groups of said dicarboxylic acid may be from about 1.2:0.8 to 0.8:1.2 but is preferably about 1:1.

The monomers of this invention which are represented by Formula (1), are prepared from polyfunctional isocyanates and hydroxyl terminated unsaturated monoesters. By the terms polyfunctional isocyanate or organic polyisocyanate as used herein is meant aromatic or aliphatic isocyanates having at least 3 isocyanate groups per molecule. Exemplary of these polyisocyanates are polymethlene polyphenyl isocyanates, such as those sold under the trade names PAPI and MONDUR MR, 4,4'4''-triphenylmethane triisocyanate; 2,4,6-toluene triisocyanate; 4,4'-dimethyl diphenyl methane 2,2',5,5'-tetraisocyanate, and condensation products of diisocyanates preferably aromatic diisocyanates with water, and polyols including diols, triols, hexitols and alkylene oxide derivatives (ethers) of these polyols to yield polyisocyanates containing 3 or more free NCO groups. These polyisocyanates and processes for the preparation thereof are known in the art as exemplified by the disclosures of German Pat. No. 1,150,518; British Pat. No. 840,500; and U.S. Pat. NOS. 3,261,655 and 3,219,598. In a preferred group of polyisocyanates the number of free isocyanate groups per molecule will be between 3 and 6. To illustrate the structure of these isocyanates the following typical formulas of polyisocyanates are presented:

(a) 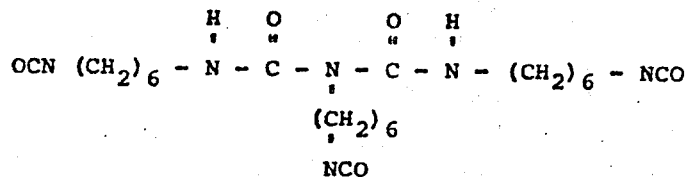

(b) 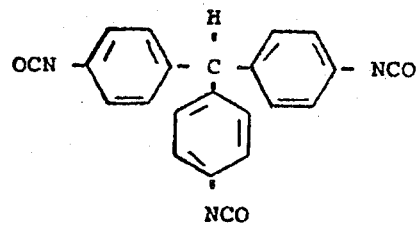

(c) 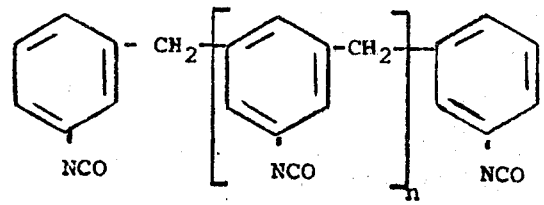

n = An Average of at least 1.0

(d) 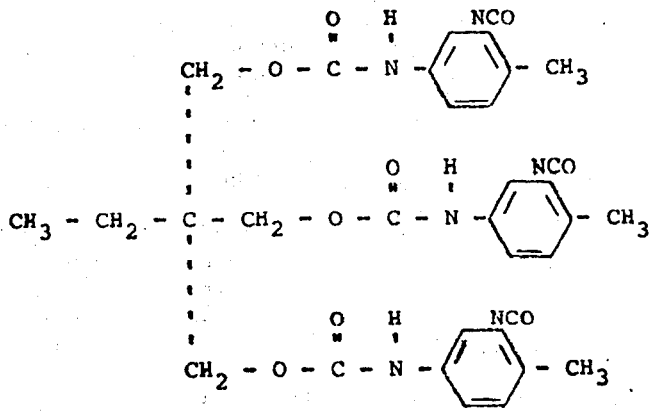
(e) 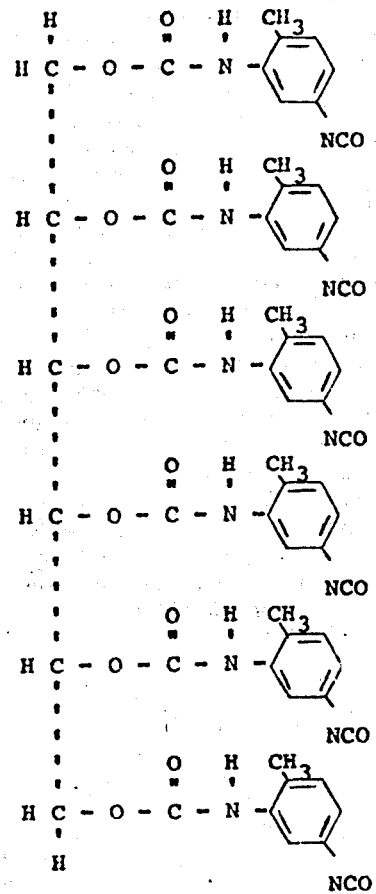
(f) 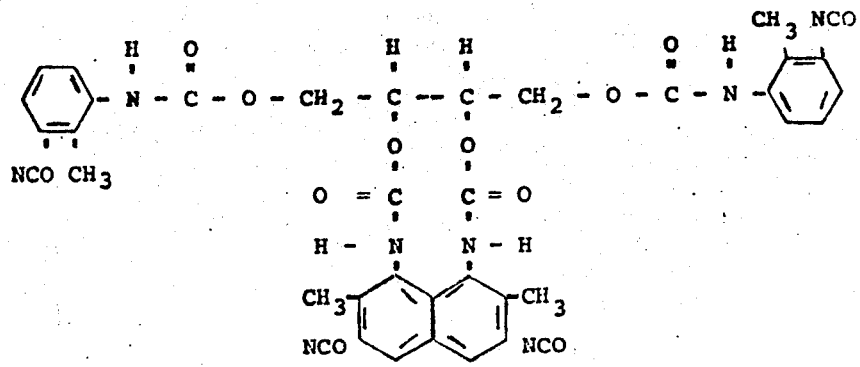

Compounds (a), (b), (c) and (d) are known respectively by the trade names Desmodur N, Mondur R, PAPI and Mondur CB.

Polyisocyanate (e) is prepared by reacting an excess (50% excess) of toluene 2,4-diisocyanate (2,4-tolylene diisocyanate) with sorbitol in a nitrogen atmosphere at a temperature between about 70° C. to 80° C. The unreacted (excess) diisocyanate is removed by extraction with Stoddard solvent. Polyisocyanate (f) is prepared by reacting erythritol with a 50% excess of toluene 2,6-diisocyanate in a nitrogen atmosphere at a temperature of about 75° C. to 80° C. and the unreacted diisocyanate is extracted with Stoddard solvent.

The hydroxyl terminated ethylenically unsaturated esters used to prepare the monomers of Formula (1) above are monohydroxyl terminated ethylenically unsaturated esters and can be made by condensing any one of a large variety of ethylenically unsaturated acids with a suitable diol reactant.

In general the preparation of the present hydroxyl terminated unsaturated ester is carried out by condensing a suitable unsaturated acid with a small molar excess of a suitable diol. For example, a mol ratio of diol to acid of from about 1.1:1 to 1.3:1 can be used but a ratio of diol to acid of about 1:1 is preferred. In the preparation of the subject monoester the condensation reaction between the diol and acid can be carried out in the presence of a catalytic amount of any of the well known condensation or esterification catalysts such as p-toluene-sulfonic acid. Such a catalyst is generally used at a concentration of from about 0.005% to 0.3% by weight based on the weight of the reaction mixture. This reaction is preferably carried out in the presence of an inert solvent to provide for solution of the reactants. For example, a hydrocarbon solvent such as toluene or xylene can be used. The present condensation reaction can be carried out at the reflux temperature of the reaction mixture. If desired, other reaction additives such as a polymerization inhibitor, for example hydroquinone can be used in conjunction with the subject reaction.

When an acid chloride of the subject unsaturated acids is used to prepare the present hydroxyl terminated ethylenically unsaturated esters, it is preferred that the mol ratio of diol to acid chloride be about 1:1 and no condensation catalyst is needed.

The ethylenically unsaturated monocarboxylic acids that can be used to prepare the subject hydroxyl terminated unsaturated esters are any of such having from about 3 to 18 carbon atoms. For example, among those that can be used are sorbic acid, acrylic acid, methacrylic acid, crotonic acid, ricinoleic acid, oleic acid, linolenic acid, linoleic acid and eleostearic acid. The acid chlorides of these acids can also be used as reactants if desired.

The subject hydroxyl terminated unsaturated esters can also be prepared from lower alkyl ($C_1$ to $C_6$) monoesters of unsaturated dicarboxylic acids such as maleic acid and fumaric acid as well as other such acids having from 3 to 18 carbon atoms.

The diol reactants used to prepare the subject hydroxyl terminated unsaturated ester reactants can also be varied greatly. The subject diol reactant can be aliphatic or aromatic and saturated or unsaturated.

Among the aliphatic diols that can be used are the straight or branched chain alkane diols and the cycloaliphatic diols having from 2 to 12 carbon atoms. For example, among those that can be used are ethylene glycol, 1,4-butylene glycol, 1,6-hexylene glycol, neopentyl glycol, 1,4-cyclohexane dimethanol, hydroxypivalyl hydroxypivalate, 2,5-dimethyl-2,5-hexanediol tetramethyl 1,3-cyclobutanediol and 2,2-bis(bromoethyl)propane-1,3-diol.

Any of the known unsaturated aliphatic diols containing from 2 to 10 carbon atoms can also be used to prepare the subject hydroxyl terminated unsaturated ester reactants. For example, among those that can be used are the monoallyl ether of glycerin, diallyl ether of pentaerythritol, hydroxyl terminated butadiene copolymers and dimethyl hexynediol.

Among the aromatic diols that can be used to prepare the subject hydroxyl terminated unsaturated ester reactants is the diol represented by Formula (2) above.

Examples of hydroxyl terminated ethylenically unsaturated esters that can be used to prepare the urethane monomers of Formula (1) above are 1-hydroxyethyl acrylate, 1-hydroxyethyl methacrylate, 1-hydroxyhexyl oleate, polyoxypropylene(16) 2,2-bis(4-hydroxyphenyl)propane monoacrylate, polyoxypropylene(4) 2,2-bis(4-hydroxyphenyl)propane monolinolenate, 1-hydroxyneopentyl linoleate, 1-hydroxypropyl ricinoleate, 1-hydroxyethyl eleostearate, 1-hydroxyethyl methacrylate, 1-hydroxyneopentyl methacrylate and hydroxymethyl cyclohexanemethyl methacrylate.

The above described types of polyisocyanates are reacted with a suitable hydroxyl terminated ethylenically unsaturated ester reactant, as exemplified above and prepared from the above described reactants, to form the monomers of this invention represented by Formula (1) above.

The urethane monomers of the present invention are prepared by reacting a suitable polyisocyanate with a sufficient quantity of one of the above described hydroxyl terminated ethylenically unsaturated esters so that there are essentially no free isocyanate groups remaining. For example, one mol of the polyisocyanate represented by formula (a) above is reacted with three mols of one of the subject hydroxyl terminated ethylenically unsaturated esters to form a product represented by Formula (1) above and as exemplified by Formulas (g) to (k) hereinafter. The present reaction between the polyisocyanate and hydroxyl terminated ethylenically unsaturated ester is generally carried out in the presence of a catalytic amount of a suitable catalyst such as an organic tin compound, for example dibutyl tin diacetate, dibutyl tin dilaurate or an amine such as triethylenediamine. Such catalysts are generally employed at a concentration from about 0.01% to 0.5% by weight based on the weight of the reaction mixture. Other reaction aids, for example, polymerization inhibitors such as hydroquinone can also be used in the preparation of the subject urethane monomers. The subject reaction used to prepare the present urethane monomers is generally carried out at a temperature within the range of 40° C. to 100° C. at atmospheric pressure in an inert atmosphere such as nitrogen. In any event the reaction temperature must be sufficient so as to drive the reaction to completion.

Unsaturated monomers representative of the monomers characterized by Formula (1) are as follows:

(g) 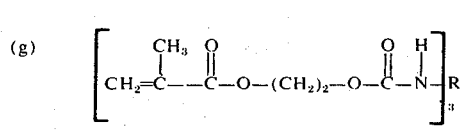

wherein R represents the trivalent residue of Desmodur N after reaction of its 3 NCO groups (h) 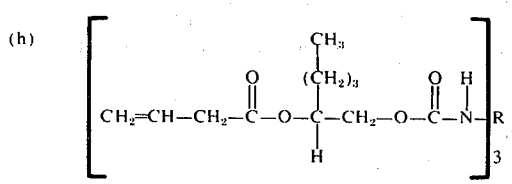

wherein R represents the trivalent residue of Mondur R after reaction of its 3 NCO groups (i) 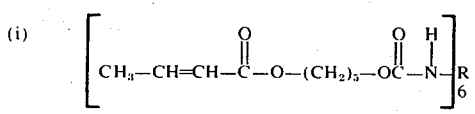

wherein R is the hexavalent residue of polyisocyanate (e) listed above after reaction of its 6 NCO groups (j) 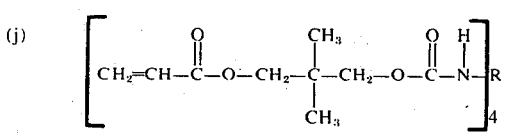

wherein R is the tetravalent residue of polyisocyanate (f) listed above after reaction of its 4 NCO groups (k) 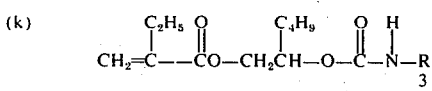

wherein R is the trivalent residue of PAPI after reaction of its 3 NCO groups.

In order for those skilled in the art to more fully understand this invention, the following non-limited examples are given.

Examples 1 to 10 illustrate the preparation of several preferred unsaturated resin monomers of the present invention.

EXAMPLE 1

280 grams of styrene, 594.6 grams of the polyisocyanate of Formula (a) (Desmodur N), 1.4 grams of hydroquinone, and 1.5 grams of dibutyl tin dilaurate are charged at room temperature to a 3-liter 4-necked flask, equipped with a stirrer, thermometer, nitrogen gas inlet tube, dropping funnel and a condenser. The temperature is then raised to a temperature of about 45° to 50° C. and maintained at this temperature and within an hour period 523.6 grams of 1-hydroxyethyl methacrylate is added dropwise. The temperature is maintained at 45° to 50° C. until the reaction product is found to be essentially free of unreacted isocyanate groups, that is, less than 0.1 percent by weight of the isocyanate groups originally present are still available or free. The styrene solution of this unsaturated urethane trisethyl methacrylate monomer resin is a clear solution.

The percent free isocyanate (NCO) content as given above and in all of the following examples were determined according to the test procedure described in the Union Carbide Corp. publication entitled "Urethane Coatings Chemicals", Copyright 1964, F-41146, pages 24 and 25.

For illustration purposes the preparation of the monomer product of Example 1 can be represented by the following equation:

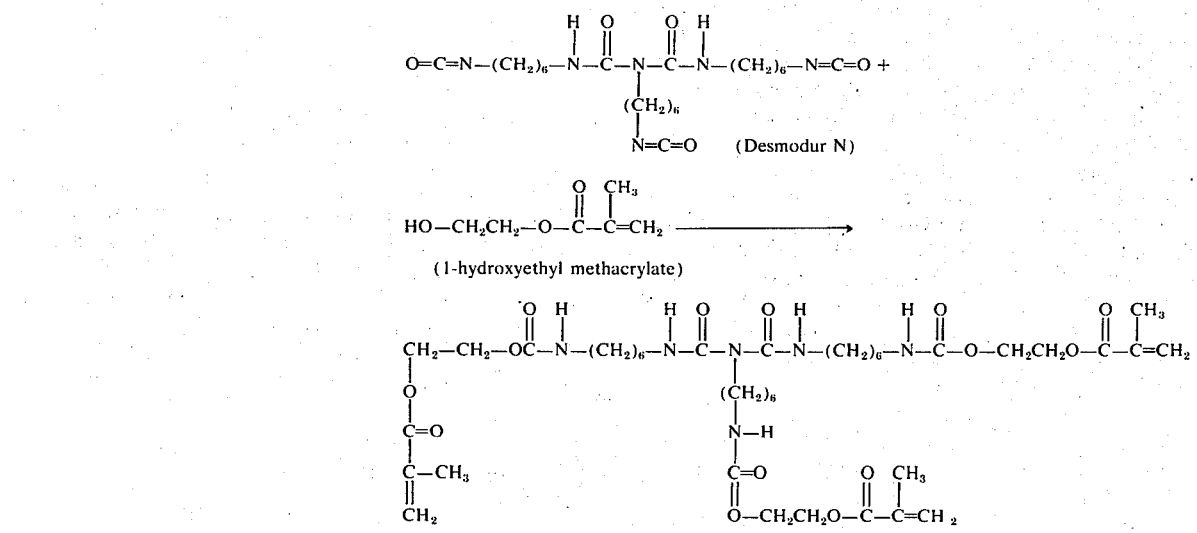

EXAMPLE 2

177.5 grams of neopentyl glycol, 122.5 grams of methacrylic acid, 0.15 gram of hydroquinone and 1.5 grams of p-toluene-sulfonic acid are charged to a one liter, 4-necked reaction vessel equipped with a stirrer, thermometer, nitrogen gas inlet tube and a water trap condenser combination. At this point, 200 grams of xylene are poured through the condenser so as to fill the water trap. Any excess xylene is allowed to flow into the reaction vessel. The mixture is then heated to its reflux temperature and the reaction allowed to proceed at reflux until the theoretical amount of water (25.6 milliliters) is obtained. The resulting 1-hydroxyneopentyl methacrylate-xylene blend is then washed repeatedly with water to remove the catalyst and the hydroquinone. The xylene is removed by vacuum distillation.

Then 169.6 grams of the resulting ester (1-hydroxyneopentyl methacrylate) product is charged according to Example 1 to a 3 liter, 4-necked reaction vessel. To this ester is added 470.4 grams of the polyisocyanate represented by Formula (a) (Desmodur N), 160 grams of sytrene as well as 0.4 gram of hydroquinone and 0.5 gram of dibutyl tin dilaurate. The reaction mixture is then heated at a temperature of from 70° to 85° C. and maintained at this temperature until the percent of free isocyanate groups drops below 0.5% by weight of the isocyanate groups originally present in the reaction mixture. The reaction product is a viscous, clear solution of the polyurethane-hydroxyneopentyl methacrylate product.

EXAMPLE 3

173 grams of 1,4-cyclohexanedimethanol, 104.5 grams of methacrylyl chloride, 40 grams of sodium hydroxide, 100 grams of distilled water, 0.2 gram of hydroquinone, and 200 grams of toluene are charged to a 1-liter, 4-necked reaction vessel equipped with a condenser, thermometer and nitrogen inlet tube. The reaction is carried out at the reflux temperature of the reaction mixture. After the completion of the reaction, the product, hydroxymethylcyclohexanemethyl methacrylate is separated from the toluene and water by distillation.

234.5 grams of the above prepared ester product is then reacted according to the procedure of Example 2 with 255.5 grams of a polyisocyanate corresponding to Formula (d) above (Mondur CB) in the presence of 0.35 gram of hydroquinone and 1.0 gram of triethylene diamine. The reaction is carried out at 70° to 85° C. until a test for free isocyanate groups shows none present. The resulting monomer product can be presented by the following formula:

hydroxypivalyl hydroxy-pivalate in the presence of 100 grams of xylene are reacted at 80° to 100° C. until the theoretical amount of HCl of esterification is removed and the corresponding hydroxyl terminated ethylenically unsaturated ester is formed as represented by the formula:

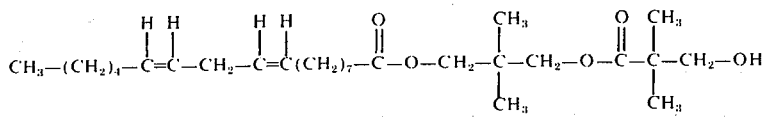

According to the procedure of Example 2, 1398 grams of the ester prepared above and 369 grams triphenylmethane triisocyanate [Formula (b) above, Mondur R] are reacted at 50° to 70° C. until the reaction mixture is found to have less than 0.5% by weight of the isocyanate groups originally present in the reaction mixture. The resulting product is a highly viscous, resinous product.

EXAMPLE 5

130 grams of the half ester of fumaric acid and methanol are reacted with 144 grams of tetramethyl 1,3-cyclobutanediol according to the procedure of Example 2 at their reflux temperature until the theoretical water of esterification has been recovered and the following product is formed:

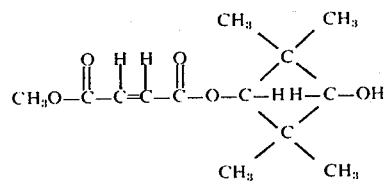

211.2 grams of the above prepared hydroxyl terminated ethylenically unsaturated ester is reacted with 109 grams of polymethylene polyphenyl isocyanate with an equivalent weight of 132 [known under the tradename of PAPI and represented by Formula (c) above] at a temperature of 80° to 85° C. in a one liter, 4-necked flask until the reaction product is essentially free of free isocyanate groups, that is, there is less than 0.5 weight percent free isocyanate present based on the original isocyanate group present in the reaction mixture. The resulting monomer is a viscous liquid.

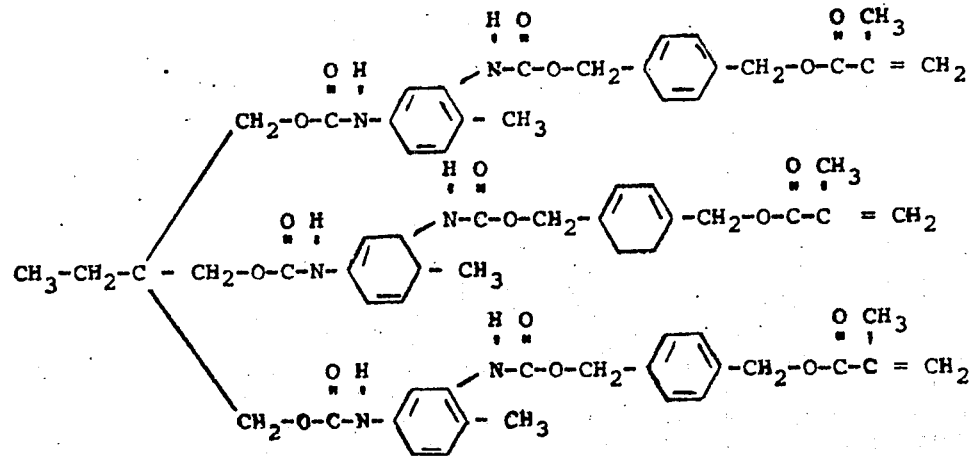

EXAMPLE 4

According to the procedure of Example 3, 298.5 grams of linoleic acid chloride and 204.3 grams of

EXAMPLE 6

To a 4-necked, 2 liter flask equipped with mechanical stirrer, nitrogen inlet tube, thermometer, condenser and water trap, 520 grams of monomethylester of fumaric acid, 576 grams of tetramethyl-1,3-cyclobutanediol, 500 grams of xylene and 1 gram of p-toluenesulfonic acid are charged at room temperature. After 72 ml of water have been collected in the water trap, the resulting fumaric acid diester of methanol and tetramethyl-1,3-cyclo-butanediol is washed to remove the catalyst and then stripped free of xylene. Then 1080 grams of the above prepared fumaric diester, 400 grams of butyl methacrylate, and 2 grams of zinc naphthenate are charged to a suitable 4-necked, round bottom flask equipped with stirrer, gas inlet tube, thermometer, condenser and the mixture is slowly heated to 60° C. under a nitrogen atmosphere. Then 520 grams of Mondur R (triphenylmethane triisocyanate) is added over a 1 hour period. The reaction is terminated when the percent free isocyanate group (NCO) content is below 0.5% by weight of the isocyanate groups originally present in the reaction mixture. The unsaturated urethane is a 80% solution in butyl methacrylate. The solution is clear and viscous.

EXAMPLE 7

To a 1 liter, 4-necked round bottom flask are charged 163.0 grams neopentyl glycol, 437 grams linolenic acid and 0.3 gram hydroquinone. The flask is equipped with mechanical stirrer, thermometer, gas inlet tube, and condenser. The reaction mixture is heated to 210° C. under a nitrogen atmosphere until the acid value of the mixture is below 2. The resulting neopentyl glycol monolinolenate is an oily liquid, of light yellow color and has a viscosity of 250 cps at 25° C. The hydroxyl number of the unsaturated monohydroxy ester is 125.

Then to a second 1 liter round bottom flask equipped with mechanical stirrer, gas inlet tube, thermometer, condenser and dropping funnel is charged 178.8 grams of the neopentyl glycol monolinolenate. The hydroxy ester is heated to 60° C. under a nitrogen atmosphere. Then over a 1 hour period 181.2 grams of PAPI (polymethylene polyphenyl isocyanate) is added from the dropping funnel. The exothermic reaction mixture is maintained at 60°–70° C. and when all the PAPI is added the temperature is increased to 100° C. for 1 hour after which time the free isocyanate group content is less than 0.5% by weight of the isocyanate groups originally present in the reaction mixture. The unsaturated urethane monomer is a dark brown, viscous resin.

EXAMPLE 8

To a 1 liter, 4-necked round bottom flask equipped with stirrer, nitrogen inlet, thermometer, condenser and Dean Stark water trap is charged 540 grams of polyoxypropylene(16)-2,2'-bis(4-hydroxyphenyl)propane, 36 grams of acrylic acid, 0.5 gram of p-toluenesulfonic acid and 100 grams of xylene and heated to reflux under a nitrogen atmosphere until the corresponding unsaturated monoester is formed. When the theoretical amount of 9 ml water is obtained the xylene is then stripped. The resulting monoester is an oily liquid. Then to a 1 liter, 4-necked round bottom flask equipped with stirrer, nitrogen inlet, thermometer, and condenser, and dropping funnel is charged 180 grams of styrene and 68.4 grams of the isocyanate represented by Formula (d) above and 1 gram of dimethylethanolamine. When the isocyanate is dissolved, the reaction mixture is heated to 60° C. under a nitrogen atmosphere over a 1 hour period. Then 351.6 grams of the above prepared monoester is added while the exotherm is not allowed to exceed 80° C. When the addition is complete, the reaction mixture is maintained at 80° C. until the percent free isocyanate group content is below 0.5% by weight of the isocyanate groups originally present in the reaction mixture. The unsaturated urethane solution is a clear viscous liquid. The resulting product can be represented by the following formula:

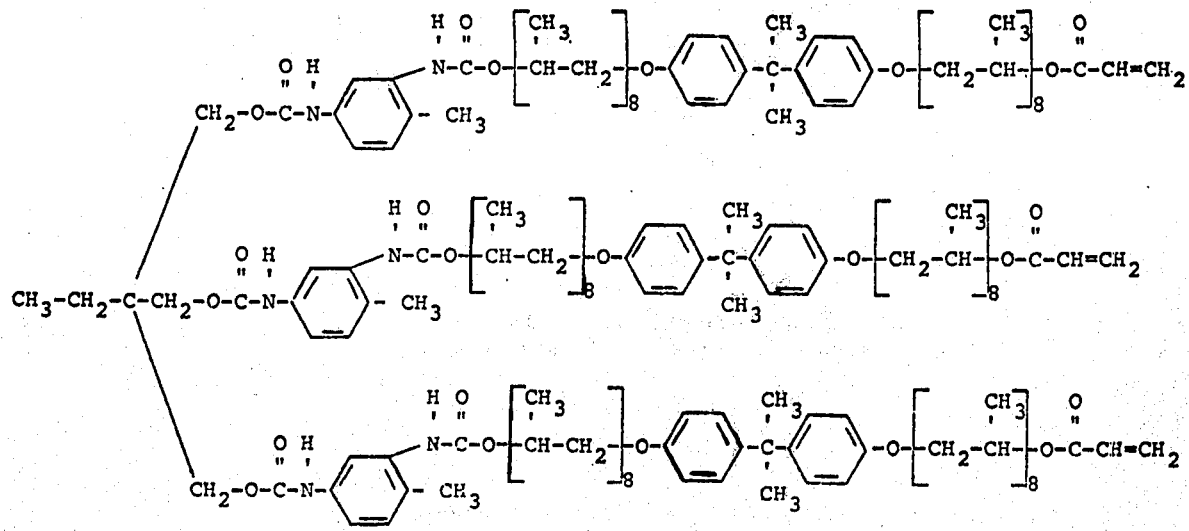

EXAMPLE 9

To a 1 liter, 4-necked, round bottom flask equipped with stirrer, nitrogen inlet tube, thermometer, water trap and condenser is charged at room temperature, 232 grams of fumaric acid, 116 grams allyl alcohol, 3 grams p-toluenesulfonic acid and 100 grams of xylene. The water trap is filled with xylene. The resulting reaction mixture is heated at reflux until 36 ml of water is collected. The product is then washed with water to remove the catalyst. Then the xylene is stripped from the reaction product mixture. The resulting monoester of fumaric acid and allyl alcohol is a water white clear liquid. The preparation of the above product can be represented by the following equation:

the percent free isocyanate group content is below 0.5% by weight of the isocyanate groups originally present. The unsaturated urethane monomer is a viscous clear resin and can be represented by the following formula:

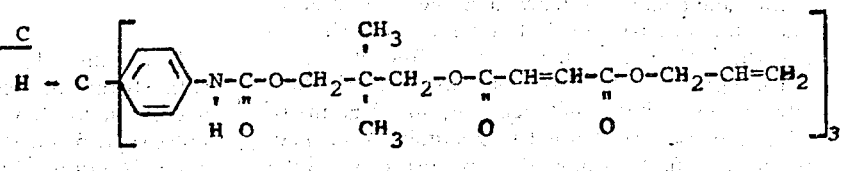

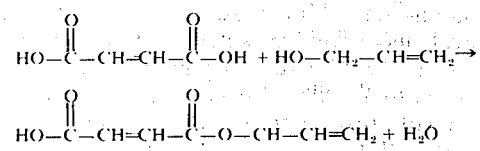

212 grams of the above prepared Product A, 208 grams of neopentyl glycol, 1 gram p-toluenesulfonic acid, 100 grams of xylene and 0.5 grams hydroquinone are charged to a 1 liter, 4-necked flask equipped with a nitrogen inlet, thermometer and condenser. The resulting mixture is refluxed until 36 ml of water is obtained. Then the xylene is stripped from the reaction product mixture. The unsaturated hydroxyester obtained is a clear, oily liquid and is represented by the following formula:

Product B

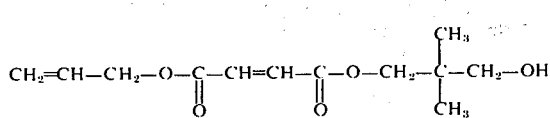

To a 1 liter, 4-necked flask equipped with stirrer, thermometer, nitrogen inlet, dropping funnel, and condenser is charged 363 grams of Product B above, 0.5 gram hydroquinone and 0.5 gram of dimethylethanolamine at room temperature. The resulting reaction mixture is slowly heated to 60° C. and within 30 minutes, 184.5 grams of Mondur R is added and the resulting mixture is maintained at a temperature from 60° C. to 80° C. When the addition is complete, the resulting mixture is heated for 1 hour at 100° C. after which time

EXAMPLE 10

To a 1 liter, 4-necked flask equipped with stirrer, nitrogen inlet, thermometer, dropping funnel and condenser is charged at room temperature 160 grams of styrene, 0.4 gram of hydroquinone, 0.4 gram dibutyl tin dilaurate and 283.2 grams of Desmodur N represented by Formula (a) above. The reaction mixture is then heated to 60° C. under nitrogen flow and within 1 hour 356.8 grams of monoallyl ether of glycerine monomethacrylate is added over a 1 hour period. Then the temperature is raised to 90° C. until the percent isocyanate group content is below 0.5% by weight of the isocyanate groups originally present. The resulting urethane monomer solution in styrene is a clear liquid and can be represented by the following formula:

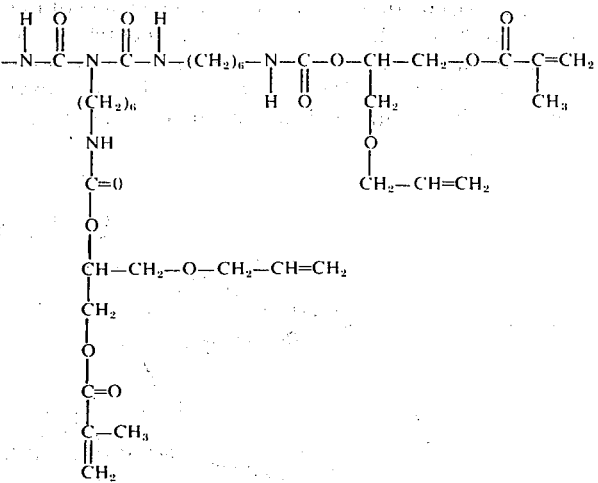

The subject urethane monomer resins and the homo and copolymer products thereof and the mixed resin products of the present invention can be used in the preparation of molded plastic products and glass fiber or other synthetic polymer fiber reinforced plastic products such as pipes, gasoline tanks, boats, duct work, storage tanks and laminates.

The mixed resin products of the present invention are comprised of the reaction products of the urethane monomers of this invention and ethylenically unsaturated polyesters, and/or other ethylenically unsaturated homopolymerizable monomers.

Examples 11 through 20 illustrate the preparation of resins, moldings and laminates using urethane monomers of this invention by themselves or in conjunction with a polyester, an ethylenically unsaturated monomer, or a combination of both. The reactants used in preparing these resinous products can be mixed by mechanical means, such as mechanical stirring, a ball mill, or other mixing or blending devices, to a uniform solution. To this mixture is then added a conventional curing system, that is, one or more catalysts and optionally promoters for an addition reaction and polymerization inhibitors if indicated. The resulting reaction mixture can be reacted at room temperature or at elevated temperature and at atmospheric pressure. In most instances, it has been found desirable to first react the subject reactants at room temperature for about 16 to 24 hours, and then post cure the resulting product at temperatures within the range of 80° C. to 175° C. for 1 to 6 hours. Obviously, these cure temperatures and reaction times can be suitably varied widely depending on the type finished product desired and its end use.

Among the ethylenically unsaturated monomers that can be copolymerized with the subject urethane monomers represented by formula (1) are any of the well known vinyl monomers such as styrene and divinylbenzene. In addition any of the other well known suitable vinyl monomers can be used, for example, acrylonitrile, glycidyl methacrylate, hydroxyalkylmethacrylate, stearylmethacrylate, tertiary butyl styrene, vinyl acetate and n-vinyl pyrrolidone. Such vinyl monomers can also be copolymerized with the copolymers resulting from the polymerization of a urethane monomer of the present invention with a suitable unsaturated polyester resin as described hereinabove.

The resin or polymer products of the present invention can contain monomer units derived from any of the hereinabove described monomers and polymers. For example, the polymerizable unsaturated urethane compounds represented by Formula (1) above can be homopolymerized or copolymerized with any ratio or mixture of monomers coming within Formula (1). Other resin products of the present invention can contain 0.5% to 95% of polymer segments derived from suitable ethylenically unsaturated polyester resins, as described hereinabove, and 0.5% to 95% of polymer segments derived from one or more of the unsaturated urethane monomers represented by Formula (1) above. In addition, the resin products of the present invention include those prepared from any combination of the above described monomers or resins in combination with sufficient quantity of a suitable vinyl monomer so that up to 50% of the resulting polymer segments are derived from said vinyl monomer, such as illustrated above, for example styrene.

Any of the well known catalysts or curing systems conventionally used in the addition polymerization of ethylenically unsaturated monomers such as herein involved can be utilized to prepare the subject homo and copolymeric resin products. For example, catalytic amounts of catalysts such as benzoyl peroxide, tertiary butyl peroxide and methyl ethyl ketone peroxide can be used. These catalysts are generally used at a concentration of from about 0.5% to 3.0% based on the weight of the reactants. Reaction promoters such as dimethyl aniline and cobalt naphthenate can be utilized in catalytic amounts along with one of the above-mentioned catalysts. In addition any of the other well known reaction modifiers can be incorporated with the subject reaction mixtures when indicated. For example, a reaction inhibitor such as tertiary butyl catechol can be used.

EXAMPLE 11

Copolymer of Monomer of Example 1 with Styrene

In a polyethylene cup, 75 grams of the monomer resin solution of Example 1, 25 grams styrene, 1 gram benzoyl peroxide and 0.2 gram of dimethylaniline are mixed together with a spatula. The water white clear solution has a viscosity at 25° C. of 77 cps. After deaerating the solution is poured into a ⅛ in. glass mold and cured at room temperature for 24 hours, followed by a postcure at 100° C. for 4 hours.

The catalyzed solution had a gel time of 7 minutes, a gel to peak time of 9-minutes, and a peak exotherm temperature of 210° C. as determined by the SPI method. This SPI method for reactivity rate or cure time is described in "The Society of the Plastics Industry Inc. book of Reinforced Plastics" by Samuel Oleesky and J. G. Mohr, Reinhold Publishing Co. 1964. The cured casting had the following properties:

| | |
|---|---|
| Flexural strength, $^{(1)}$ PSI | 17,200 |
| Flexural modulus, $^{(2)}$ $10^6$ | 0.41 |
| Barcol hardness$^{(3)}$ | 28–31 |
| Heat distortion, $^{(4)}$ °C. | 95 |
| Tensile strength, $^{(5)}$ PSI | 10300 |
| Tensile modulus, $^{(6)}$ $10^6$ | 0.42 |
| Percent Elongation $^{(7)}$ | 8.87 |
| Charpy impact$^{(8)}$ | 6.77 |
| $^{(1)}$ ASTM D-790-70 | $^{(5)}$ ASTM D-638-68 |
| $^{(2)}$ ASTM D-790-70 | $^{(6)}$ ASTM D-638-68 |
| $^{(3)}$ ASTM D-2583-67 | $^{(7)}$ ASTM D-638-68 |
| $^{(4)}$ ASTM D-648-56 | $^{(8)}$ ASTM D-256-70 |

EXAMPLE 12

Copolymer of Monomer of Example 1 with Styrene and Polyoxypropylene(2.2)-2,2'-bis(4-Hydroxyphenyl)-Propane Fumarate In a polyethylene cup, 25 grams of a mixture of 50% polyoxypropylene(2.2)-2,2'-bis(4-hydroxyphenyl)propane fumarate and 50% styrene, plus 28.1 grams styrene and 46.9 grams of the unsaturated urethane solution of Example 1, 1 gram benzoyl peroxide and 0.2 gram of dimethyl aniline are thoroughly mixed. This solution at 50% solids has a viscosity of 81 cps. at 25° C. and is yellowish. After deaerating, the mixture is poured into a ⅛ in. glass mold, cured for 24 hours at room temperature and post cured 4 hours at 100° C. The casting had the following properties as determined by the same ASTM tests used to evaluate the product of Example 11:

| | |
|---|---|
| Flexural Strength PSI | 16100 |
| Flexural modulus, $10^6$ | 0.41 |
| Barcol Hardness | 20–23 |
| Heat Distortion °C. | 97 |
| Tensile Strength, PSI | 9900 |
| Tensile Modulus, $10^6$ | 0.43 |
| Percent Elongation | 8.50 |
| Charpy Impact | 5.51 |

EXAMPLE 13

Copolymer of Monomer of Example 1 with Styrene and Polyoxypropylene(2.2)-2,2'-bis(4-Hydroxyphenyl)-Propane Fumarate In a polyethylene cup, 50 grams of a mixture of 50% polyoxypropylene(2.2)-2,2'-bis(4-hydroxyphenyl)propane fumarate and 50% styrene, plus 18.7 grams styrene, 31.3 grams of the unsaturated urethane solution of Example 1, 1 gram benzoyl peroxide and 0.2 gram dimethyl aniline are thoroughly mixed. At 50% solids this solution has a viscosity of 158 cps at 25° C. and the following cure times as determined by the SPI method or reactivity test referred to hereinabove: gel time 26 minutes, gel to peak time 12 minutes, peak temperature 216° C. After deaerating, the catalyzed solution is poured into a ⅛ in. glass mold and cured for 24 hours at room temperature and post cured 4 hours at 100° C. The casting had the following properties as determined by the same ASTM tests used to evaluate the product of Example 11:

| | |
|---|---|
| Flexural Strength, PSI | 19300 |
| Flexural Modulus, 10⁶ | 0.45 |
| Barcol Hardness | 31–33 |
| Heat Distortion °C. | 107 |
| Tensile Strength, PSI | 10700 |
| Tensile Modulus, 10⁶ | 0.44 |
| Percent elongation | 4.86 |
| Charpy impact | 5.08 |

EXAMPLE 14

Homopolymer of Monomer of Example 3

In a polyethylene cup, 100 grams of the monomer resin of Example 3 is mixed with 1.5 grams of a 60% solution of methyl ethyl ketone peroxide in dimethyl phthalate, 1% cobalt naphthenate, 0.2 gram dimethylaniline and 0.04 gram tertiary butyl catechol. The mixture had the following cure times as determined by the SPI method referred to hereinabove: gel time 40 minutes, gel to peak time 11 minutes, and peak exotherm 209° C. After deaerating, the catalyzed urethane monomer is poured in a ⅛ in. glass mold, cured for 24 hours at room temperature and 4 hours at 100° C. The casting is a tough, clear, thermoset plastic.

EXAMPLE 15

Homopolymer of Monomer of Example 5

In a polyethylene cup, 100 grams of the monomer resin of Example 5 is mixed with 2 grams of benzoyl peroxide. The deaerated catalyzed mixture is poured into a glass mold having a depth of ⅛ in. and cured for 1 hour at 60° C., followed by 1 hour at 90° C. and followed by 1 hour at 150° C. The cured thermoset casting is clear and has a dark brown color.

EXAMPLE 16

Copolymer of Styrene Solution of Monomer of Example 1 and a Butyl Methacrylate Solution of the Monomer of Example 6

In a polyethylene cup, 50 grams of unsaturated urethane solution in styrene of Example 1 and 50 grams of unsaturated urethane solution in butyl methacrylate of Example 6 are mixed together with 1.0 gram benzoyl peroxide and 0.2 gram of dimethyl aniline. The mixture is poured into a ⅛ in. glass mold, cured for 24 hours at room temperature and post cured for 4 hours at 100° C. After curing, a clear transparent glass-like thermoset casting is obtained.

EXAMPLE 17

Laminate of Copolymer of Polyoxypropylene(2.2)-2,2'-bis(4-Hydroxyphenyl)-Propane Fumarate, Styrene and Monomer of Example 1

A laminate is prepared by copolymerizing a 50% solution of polyoxypropylene(2.2)-2,2'-bis(4-hydroxyphenyl)propane fumarate in styrene with the monomer resin solution of Example 1 and styrene following the SPI lay-up method (as described under ASTM-C-581-68) of 1 layer Owens Corning Fiberglass (C-glass), 2 layers fiber glass chopped strand (E-glass) mat, and 1 layer C-glass. The laminate is made between 2 layers of Mylar polyester film. In a suitable container, 195.2 grams of a mixture of 50% polyoxypropylene(2.2)-2,2'-bis(4-hydroxyphenyl)propane fumarate and 50% styrene plus 220 grams of styrene, 367 grams resin solution of Example 1, 3.9 grams of benzoyl peroxide and 1.17 grams of dimethyl aniline are mixed. The glass/resin laminate was prepared from this solution and a combined weight of C-glass and chopped mat of 237 grams. The laminate was cured for 24 hours at room temperature and 4 hours at 100° C. The laminate had the following properties as determined by the same ASTM tests used to evaluate the product of Example 11:

| | |
|---|---|
| Percent glass[1] | 26% |
| Tensile strength PSI | 13400 |
| Tensile modulus 10⁶ | 0.98 |
| Percent break elongation | 2.03 |
| Flexural strength PSI | 15700 |
| Flexural modulus 10⁶ | 0.74 |
| Barcol hardness | 35–40 |

[1] ASTM-D-2584-67T

EXAMPLE 18

Molding Compound Copolymer of Monomer of Example 7, Styrene and Divinyl benzene 72.13 grams of the monomer resin of Example 7 are mixed with 11.5 grams of styrene and 10 grams divinylbenzene. To this solution then is added 0.03 gram of ditertiarybutylhydroquinone, 0.28 gram of benzoyl peroxide, 0.94 gram of tertiarybutyl perbenzoate, 0.47 gram triphenyl phosphite and 4.66 grams of aluminum stearate.

39.2 grams of the above mixture are then blended with 30.8 grams calcium carbonate Surfex MM, and 30 grams Owens Corning ½ in. chopped glass fibers. The resulting molding compound was molded into ⅛ in. thick pieces at 300° F. under 2000 psi pressure. The molded plastic (per the above noted ASTM tests — Example 11) had a Barcol hardness of 70, flexural strength = 17000 PSI, flexural modulus = 1.6–10⁶, tensile strength = 8000 PSI, Izod impact = 12 and HDT (Heat Distortion Temperature) > 300° F.

EXAMPLE 19

Copolymer of Monomer of Example 9 With Polyoxypropylene(2.2)-2,2'-bis(4-Hydroxyphenyl)-Propane Fumarate and Styrene To a polyethylene cup is charged 40 grams of the monomer resin of Example 9, 50 grams of a mixture of 50% polyoxypropylene(2.2)-2,2'-bis(4-hydroxyphenyl)propane fumarate and 50% styrene plus 10 grams of styrene, 1 grams of benzoyl peroxide and 0.1 gram of dimethyl aniline and mixed thoroughly. Then after deaerating, the mixture is poured into a ⅛ in. glass mold and cured for 24 hours at room temperature followed by 4 hours at 100° C. The resulting casting is a tough, clear thermoset resin.

EXAMPLE 20

Copolymer of Monomers of Examples 10 and 3 and Styrene

In a polyethylene cup is mixed the following: 50 grams of the monomer resin of Example 10, 10 grams of styrene and 40 grams of the monomer resin of Example 3, 1.2 grams benzoyl peroxide, 0.1 gram dimethyl aniline. Then after deaerating, the mixture is poured into a glass mold having a depth of ⅛ in. and cured at room temperature for 1 hour and 4 hours at 100° C. The resulting casting is a clear transparent plastic.

I claim:

1. A polymer comprising the polymerization product of a polymerizable urethane compound having the structure

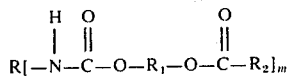

wherein R is a residue of a polyfunctional organic isocyanate which contained at least m isocyanate groups, m is at least about 3, $R_1$ is a radical resulting from the removal of 2 hydroxyl groups from an etherified diphenol and $R_2$ is an alkenyl radical containing from about 2 to 18 carbon atoms.

2. A compound of claim 1 wherein the etherified diphenol is represented by the formula:

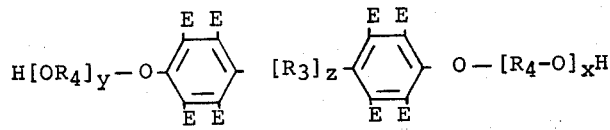

wherein z is 0 or 1; $R_3$ is an alkylene radical containing 1 to 5 carbon atoms, oxygen, sulfur or a divalent radical which may be represented by the following formulae:

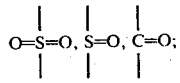

$R_4$ is ethylene or propylene; each E is individually selected from the hydrogen atoms and halogen atoms, and x and y are integers from 1 through about 20 with the proviso that the sum of x and y is from about 2 through about 30.

3. A polymer of claim 2 wherein the etherified diphenol is an oxyalkylated 4,4'-isopropylidenediphenol.

4. A polymer of claim 2 wherein the etherified diphenol is polyoxypropylene (2.2)-2,2-bis(4-hydroxyphenyl) propane.

5. A polymer comprising the polymerization product of a polymerizable urethane compound having the structure

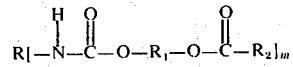

wherein R is a residue of a polyfunctional organic isocyanate which contained at least m isocyanate groups, m is at least about 3, $R_1$ is a radical resulting from the removal of 2 hydroxyl groups from an etherified diphenol and $R_2$ is an alkenyl radical containing from about 2 to 18 carbon atoms and an ethylenically unsaturated monomer.

6. A polymer of claim 5 wherein the ethylenically unsaturated monomer is a vinyl monomer.

7. A polymer of claim 5 wherein the vinyl monomer is styrene.

* * * * *